US012569413B1

(12) United States Patent
Hagerty et al.

(10) Patent No.: US 12,569,413 B1
(45) Date of Patent: Mar. 10, 2026

(54) MULTIFUNCTIONAL FACIAL PATCH PRODUCT

(71) Applicant: ASO LLC, Sarasota, FL (US)

(72) Inventors: Brooke A. Hagerty, Bradenton, FL (US); Edmund A. Sinda, Bradenton, FL (US); Mira Dosen, Sarasota, FL (US)

(73) Assignee: ASO LLC, Sarasota, FL (US)

( * ) Notice: Subject to any disclaimer, the term of this patent is extended or adjusted under 35 U.S.C. 154(b) by 247 days.

(21) Appl. No.: 18/376,626

(22) Filed: Oct. 4, 2023

Related U.S. Application Data

(60) Provisional application No. 63/413,667, filed on Oct. 6, 2022.

(51) Int. Cl.
| | |
|---|---|
| *A61K 8/02* | (2006.01) |
| *A61F 7/02* | (2006.01) |
| *A61Q 19/08* | (2006.01) |
| *A61F 7/00* | (2006.01) |

(52) U.S. Cl.
CPC .............. *A61K 8/0208* (2013.01); *A61F 7/02* (2013.01); *A61Q 19/08* (2013.01); *A61F 2007/0003* (2013.01); *A61F 2007/0095* (2013.01); *A61F 2007/0226* (2013.01); *A61F 2007/0257* (2013.01); *A61K 2800/244* (2013.01); *A61K 2800/438* (2013.01); *A61K 2800/45* (2013.01)

(58) Field of Classification Search
CPC ............ A61K 8/0208; A61K 2800/244; A61K 2800/438; A61K 2800/45; A61F 7/02; A61F 2007/0003; A61F 2007/0095; A61F 2007/0226; A61F 2007/0257; A61Q 19/08
See application file for complete search history.

(56) References Cited

U.S. PATENT DOCUMENTS

| | | | |
|---|---|---|---|
| 4,325,254 A | 4/1982 | Svacina et al. | |
| 5,135,518 A | 8/1992 | Vera | |
| 5,181,905 A | 1/1993 | Flam | |
| 5,366,491 A | 11/1994 | Ingram et al. | |
| 5,630,959 A | 5/1997 | Owens | |
| 5,817,149 A | 10/1998 | Owens | |
| 6,235,047 B1 | 5/2001 | Augustine et al. | |
| 6,336,935 B1 | 1/2002 | Davis et al. | |
| 7,238,196 B2 | 7/2007 | Wibaux | |
| 7,934,495 B2 | 5/2011 | Goldenberg | |
| 2003/0167556 A1* | 9/2003 | Kelley ................ | A45D 44/002 2/206 |

(Continued)

OTHER PUBLICATIONS

Hagerty et al.—Cold Hydrogel Skin Patch, U.S. Appl. No. 18/376,600, filed Oct. 4, 2023.

(Continued)

*Primary Examiner* — Tigist S Demie

(74) *Attorney, Agent, or Firm* — GrayRobinson, P.A.

(57) ABSTRACT

A facial patch product includes a hydrocolloid patch, a hydrogel patch, and a silicone patch. The hydrocolloid patch has a hydrocolloid patch outer layer that forms a physical barrier over a hydrocolloid layer attached to the hydrocolloid patch outer layer. The hydrogel patch has a hydrogel patch outer layer that forms a physical barrier over a hydrogel layer attached to the hydrogel patch outer layer. The hydrocolloid patch, hydrogel patch, and silicone patch are separate from one another.

26 Claims, 9 Drawing Sheets

(56)            References Cited

U.S. PATENT DOCUMENTS

| | | | |
|---|---|---|---|
| 2010/0055161 A1* | 3/2010 | Ahn | A61Q 19/08 |
| | | | 424/617 |
| 2014/0221896 A1 | 8/2014 | Freer et al. | |
| 2019/0298038 A1* | 10/2019 | Miles | A61M 35/00 |
| 2024/0108513 A1 | 4/2024 | Hagerty et al. | |

OTHER PUBLICATIONS

Hagerty et al.—Cold Hydrogel Skin Patches, U.S. Appl. No. 18/376,612, filed Oct. 4, 2023.
Hagerty et al.—Skin Treatment Product, U.S. Appl. No. 18/376,595, filed Oct. 4, 2023.
Hagerty et al.—Tinted Skin Patches for Covering Skin Blemishes, U.S. Appl. No. 18/376,587, filed Oct. 4, 2023.

\* cited by examiner

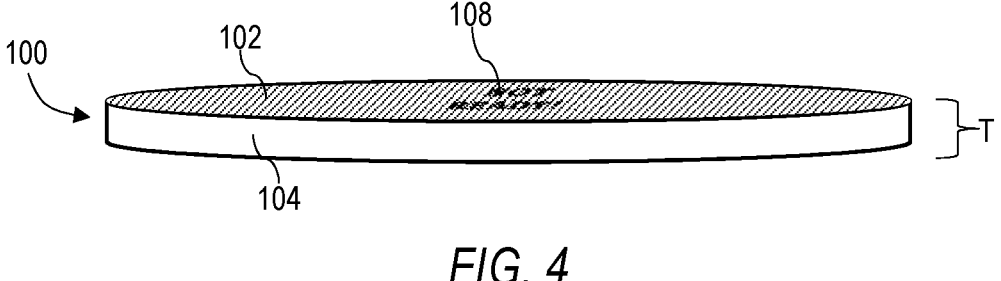
_FIG. 4_
_FIG. 5_

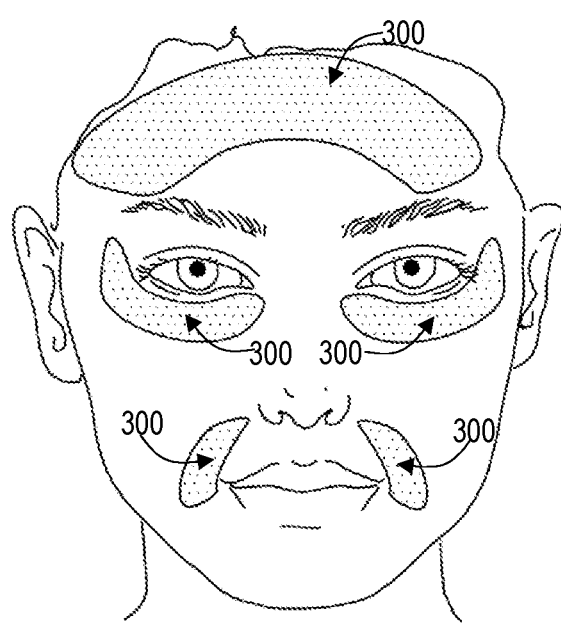
*FIG. 18*
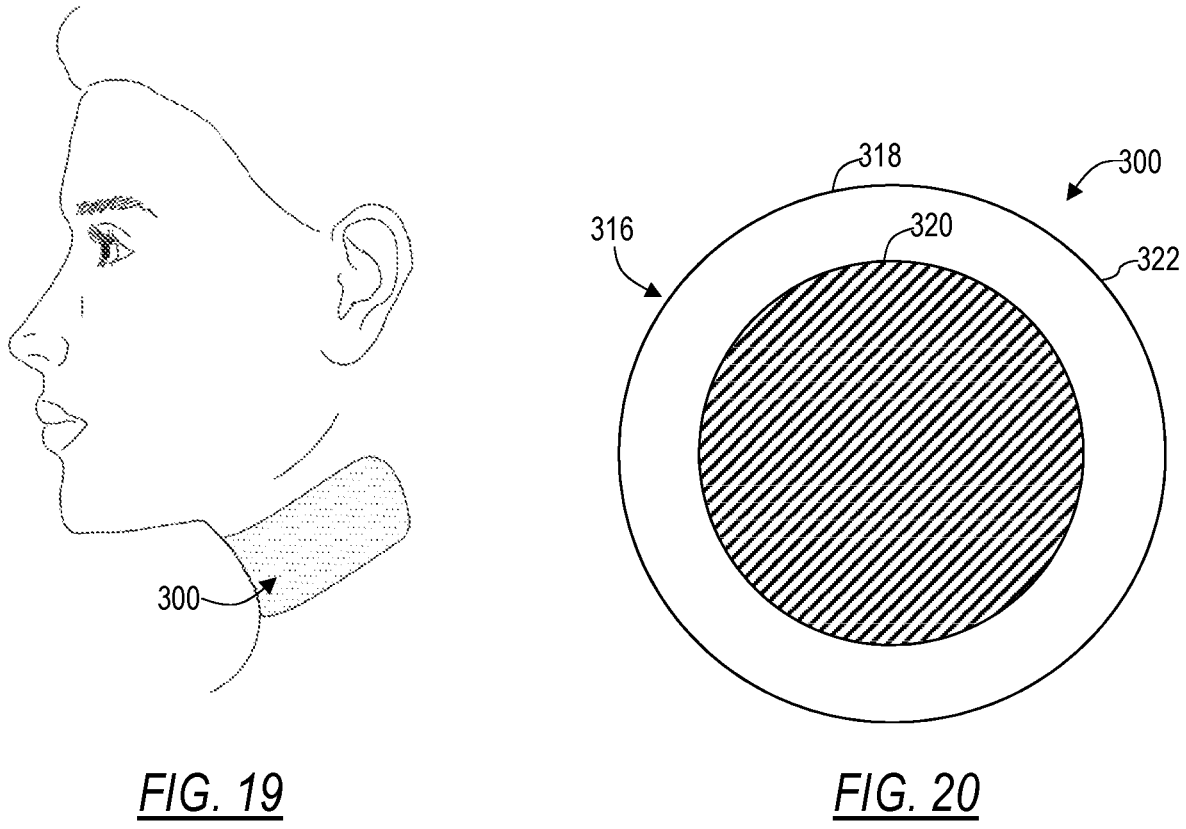
*FIG. 19*                          *FIG. 20*

MULTIFUNCTIONAL FACIAL PATCH PRODUCT

CROSS-REFERENCE TO RELATED APPLICATION

This claims the benefit of priority from Application No. 63/413,667, filed Oct. 6, 2022, which is incorporated by reference in its entirety.

FIELD

This relates to the field of beauty products, and more particularly, patches that can be applied to skin.

BACKGROUND

Facial beauty is a concern for many people. Common skin conditions people treat at home include acne, dehydration, swelling, and signs of ageing. A plethora of beauty products that target these conditions are available.

BRIEF SUMMARY

A problem with conventional beauty product patches that can be applied to skin is that they are designed to treat only a particular condition or only specific portion of the face. What is needed is a facial patch product with a combination of different types of patches that can be applied to different parts of the face for treating conditions that each part of the face is prone to having.

An example of such a facial patch product includes a hydrocolloid patch, a hydrogel patch, and a silicone patch. The hydrocolloid patch has a hydrocolloid patch outer layer that forms a physical barrier over a hydrocolloid layer attached to the hydrocolloid patch outer layer. The hydrogel patch has a hydrogel patch outer layer that forms a physical barrier over a hydrogel layer attached to the hydrogel patch outer layer. The hydrocolloid patch, hydrogel patch, and silicone patch are separate from one another.

The facial patch product may include one or more of the following features.

A first thermochromic material may be on the hydrocolloid patch and/or first waterproof packaging encapsulating the hydrocolloid patch. The first thermochromic material indicates the hydrocolloid patch is at a predetermined temperature.

The first thermochromic material may be on the hydrocolloid patch outer layer.

The first thermochromic material may be on the first waterproof packaging.

The first thermochromic material may be on the hydrocolloid patch and the first waterproof packaging may include a transparent section through which the first thermochromic material is visible from outside the first waterproof packaging.

The predetermined temperature may be 80 to 100 degrees F.

The predetermined temperature may be 105 degrees F.

A second thermochromic material may be on the hydrogel patch and/or second waterproof packaging encapsulating the hydrogel patch. The second thermochromic material may indicate the hydrogel patch is at a predetermined temperature.

The second thermochromic material may be on the second waterproof packaging.

The second thermochromic material may be on the hydrogel patch and the second waterproof packaging may include a transparent section through which the second thermochromic material is visible from outside the second waterproof packaging.

The predetermined temperature may be 20 to 55 degrees F.

The hydrogel layer may include a material that decreases a freezing point of water in the hydrogel layer.

An example of a method includes placing on a first portion of a human face a hydrocolloid patch having a hydrocolloid patch outer layer that forms a physical barrier over a hydrocolloid layer attached to the hydrocolloid patch outer layer. On a second portion of the human face, a hydrogel patch is placed. The hydrogel patch has a hydrogel patch outer layer that forms a physical barrier over a hydrogel layer attached to the hydrogel patch outer layer. On a third portion of the human face, a silicone patch is placed. The hydrocolloid patch, hydrogel patch, and silicone patch are worn at the same time.

The method may also include one or more of the following features.

A first thermochromic material may be on the hydrocolloid patch and/or first waterproof packaging encapsulating the hydrocolloid patch indicates the hydrocolloid patch is at a predetermined temperature.

The first thermochromic material may be on the hydrocolloid patch outer layer.

The first thermochromic material may be on the first waterproof packaging.

The first thermochromic material may be on the hydrocolloid patch and the first waterproof packaging may include a transparent section through which the first thermochromic material is visible from outside the first waterproof packaging.

The predetermined temperature may be 80 to 100 degrees F.

The predetermined temperature may be 105 degrees F.

A second thermochromic material may be on the hydrogel patch and/or second waterproof packaging encapsulating the hydrogel patch. The second thermochromic material indicates the hydrogel patch is at a predetermined temperature.

The second thermochromic material may be on the second waterproof packaging.

The second thermochromic material may be on the hydrogel patch and the second waterproof packaging may include a transparent section through which the second thermochromic material is visible from outside the second waterproof packaging.

The predetermined temperature may be 20 to 55 degrees F.

The hydrogel layer may include a material that decreases a freezing point of water in the hydrogel layer.

The product and method may also include any combination of these features.

BRIEF DESCRIPTION OF THE DRAWINGS

FIG. 4 is a top perspective view of a first example of a hydrocolloid patch.

FIG. 5 is an exploded view thereof.

FIG. 18 shows some of the possible locations on the face for the silicone patches.

FIG. 19 shows an example of a silicone patch on the front of a person's neck.

FIG. 20 is a top view of another example of the silicone patch.

DETAILED DESCRIPTION OF EXAMPLES

This disclosure describes examples and aspects, but not all possible examples or aspects of the facial patch product and related methods. Where a particular feature is disclosed in the context of a particular aspect or example, that feature can also be used, to the extent possible, in combination with and/or in the context of other aspects and examples. The facial patch product may be embodied in many different forms and should not be construed as limited to only the examples described here.

The facial patch product provides a solution for busy individuals who want to treat multiple skin problems on the face and/or neck at once, often overnight. The facial patch product includes at least two of the following: hydrocolloid patches, hydrogel patches, and silicone patches.

Figures 1, 2, 3:
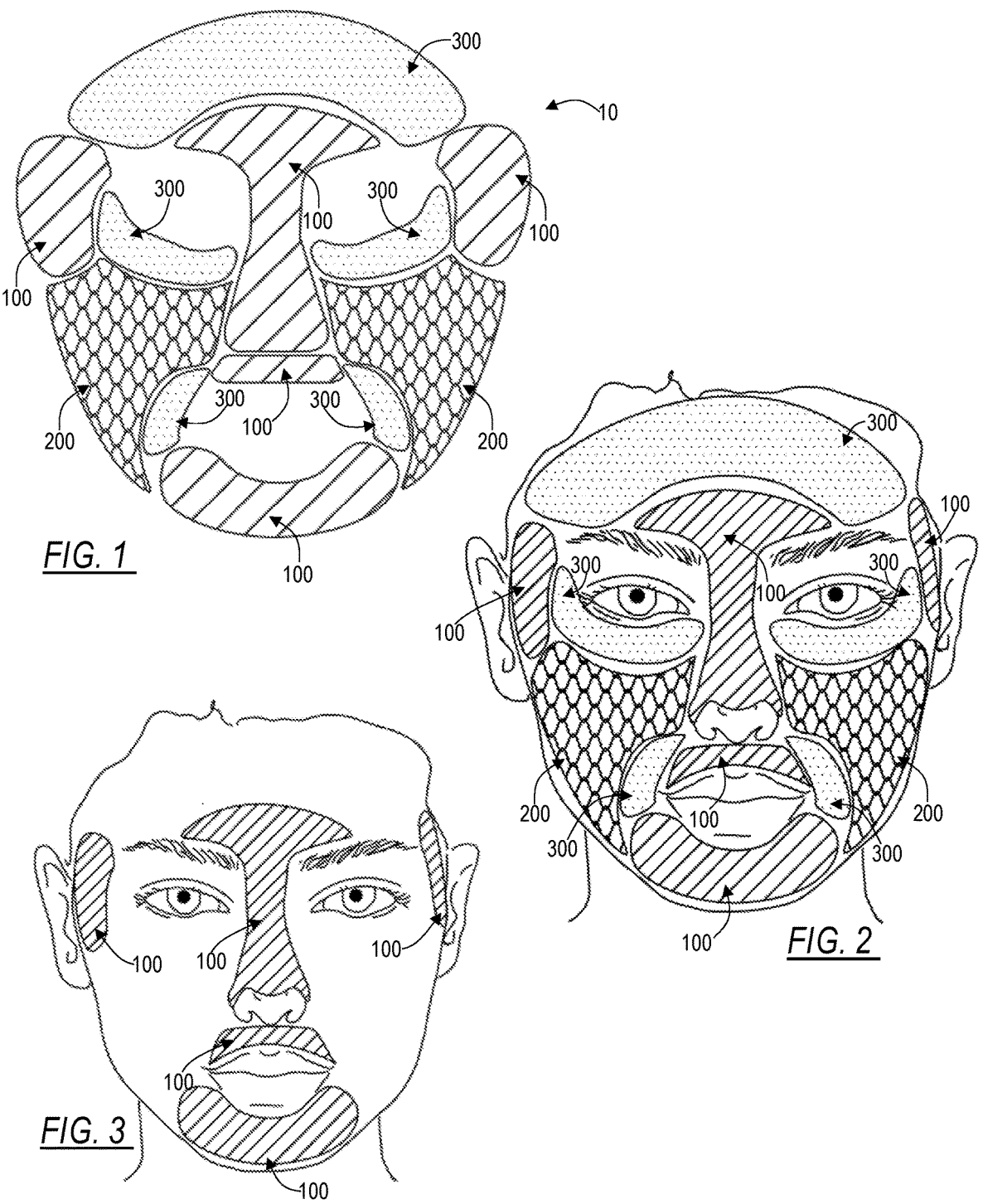
FIG. 1 is a front view of an example of some of the patches in the facial patch product.
FIG. 2 shows the patches of FIG. 1 being worn on a human face.
FIG. 3 shows some of the possible locations on the face for the hydrocolloid patches.

Referring to FIG. 1, an example of the facial patch product 10 includes a plurality of patches that may or may not interlock together. The product includes at least two of each of the following types of patches: a hydrocolloid patch 100, a hydrogel patch 200, and a silicone patch 300. In certain examples, the patches 100, 200, 300 are designed in a way that they will interlock together. In other examples, the patches 100, 200, 300 are designed in a way that they do not overlap. In some particular examples, the patches 100, 200, 300 can contour to the shape of the face.

Though the design of the patches 100, 200, 30 can vary, the purpose of the face patch product 10 is to provide more than one patch function by providing patches that are most suitable for treating particular parts of the face.

FIG. 2 shows possible facial locations for the three types of patches.

Referring to FIG. 3, hydrocolloid patches 100 are applied to locations on the face that may produce excess oils and are known for acne. Hydrocolloid patches 100 may be useful for clearing pores and absorbing sebum from blemishes. Hydrogel patches 200 are applied to locations on the face known to become dehydrated and may also contain areas in which blemishes occur deep under the skin. Hydrogel patches 200 may provide hydration and cooling, help manage soft tissue recovery, reduce swelling, and relieve pain. Silicone patches 300 are applied to locations of the face known to be in areas of skin fragility, discoloration, wrinkles, and other signs of aging. Silicone patches 300 may help regulate collagen production and create smoother and more supple skin.

Referring to FIGS. 4 and 5, an example of a hydrocolloid patch 100 includes an outer layer 102 and a hydrocolloid layer 104. The outer layer 102 may be secured to the hydrocolloid layer via an adhesive 106 applied to a surface of the hydrocolloid layer 104.

The outer layer 102 covers the underlying hydrocolloid layer 104 and protects it from external contamination. The outer layer 102 also deters exudate from leaking outside of the hydrocolloid patch 100.

The outer layer 102 layer includes a backing material suitable for use in wound dressings. Examples of such backing materials include but are not limited to, woven or nonwoven fabrics, knits, films, or the like. Backing materials used in conventional wound dressings may be used.

In certain examples, the backing material may be an opaque, translucent, or transparent polymeric elastic film.

The backing material may be flexible and conformable to different surfaces of the body. When the backing material is applied to the skin, it can conform to the shape of the skin even if the wearer moves. The backing material may be constructed in such a way that it stretches and contracts to adapt to bodily movement.

Examples of specific backing materials include, but are not limited to polyethylene, polyurethane, co-polyester, polyether block amide films, PVC, or the like.

The outer layer 102 may be waterproof and/or may be breathable with a moisture vapor transmission rate above 0%.

As an alternative to using an adhesive 106, the hydrocolloid layer 104 itself may serve as an adhesive.

The hydrocolloid material of the hydrocolloid layer 104 may be hydrophilic and form a substrate that can adhere to skin. The hydrocolloid material can absorb fluid while applied to the skin of the wearer. Whether the hydrocolloid layer 104 itself is adhesive, or whether an adhesive 106 is utilized, the hydrocolloid patch 100 may have sufficient adhesion for prolonged contact with the skin of the wearer.

Hydrocolloid materials may have a polymeric structure in which a hydrophilic polymer forms a three-dimensional cross-linked network. Hydrocolloids are able to hold water within this network.

Hydrocolloid materials may include one or more natural hydrophilic polymers such as, for example, pectins, gelatins, cellulosic materials such as carboxymethylcelluloses (CMC), collagens, dextrans, elastins, chitins, chitosans, alginates, or the like.

Hydrocolloid materials may include one or more synthetic hydrophilic polymers such as, for example, polyacrylic acids (PAA), polyvinyl alcohols, polyethylene glycols, polyvinyl pyrrolidones, polyurethanes, polyhydroxyethyl methacrylates, or the like.

Hydrocolloid materials may also include a cross-linking agent, Examples of cross-linking agents include, but are not limited, to calcium salts such as calcium chloride, calcium sulfate, calcium nitrate; zinc salts such as zinc nitrate, zinc chloride, zinc sulfate; ammonium persulfate, glutaraldehyde or the like.

The hydrocolloid material may also include a pressure sensitive adhesive, such as poly-isobutylene, or the like.

The hydrocolloid patch 100 is designed to be heated prior to applying to skin. When some hydrocolloid materials are heated, they may become too pliable to adhere to the skin sufficiently. To improve the mechanical properties of a heated hydrocolloid material, certain examples of the hydrocolloid material include a chemical agent useful in improving the heat tolerance of the hydrocolloid material. Examples of such chemical agents may include, but are not limited to, calcium chloride, sodium chloride, acetic acid, or another other agent that is known to increase the boiling point of water. Another form which may assist in reducing the adhesion of the hydrocolloid patch 100 after heating may be to reduce the amount of poly-isobutylene in the hydrocolloid layer if present.

Certain examples of the hydrocolloid patch 100 have a thickness T of 0.1 mm to 1.5 mm or 0.12 mm to 1.5 mm.

Certain examples of the hydrocolloid material may also include one or more other ingredients such as, for example, therapeutically active ingredients such as wound healing promoting compounds and antimicrobial compounds. Other ingredients may include beautifying ingredients, such as aloe, hyaluronic acid, peptides, apple cider vinegar, collagen, turmeric, green tea, Vitamin A, Vitamin C, Vitamin E, or any other combination of ingredients.

The hydrocolloid patch 100 also includes a thermochromic material 108 that reversibly changes color when heated above a temperature that causes a color or appearance transition in the thermochromic material 108. Thermochromic materials include, for example, certain liquid crystals and organic dyes, such as leuco dyes. Thermochromic materials 108 can be mixed with other materials to create unique visual effects.

Conventional thermochromic inks, thermochromic plastics, thermochromic dyes, thermochromic powders, thermochromic films, or the like may serve as the thermochromic material 108. The purpose of the thermochromic material 108 is to indicate to the wearer when the hydrocolloid patch 100 is at a predetermined temperature for placement on the skin.

In the example of FIGS. 4 and 5, the thermochromic material 108 is on the outer layer 102 in the form of a visible indicator. This example allows the thermochromic material 108 to convey a message to the wearer when it is ready for application to the skin.

The thermochromic material 108 is selected to provide an indicator relating to the temperature of the hydrocolloid patch 100. The indicator may be the appearance of a visible indicator, a color change, a thermometer, or the like. The thermochromic material 108 provides the indicator at a predetermined temperature. For example, if the predetermined temperature is 80-100 degrees F. or about 90 degrees F., the indicator may appear at 80-100 degrees F. or about 90 degrees F. In other examples, the predetermined temperature may be a temperature such as 105 degrees F. in which the hydrocolloid patch 100 is too hot to be applied to skin.

In certain examples, thermochromic material 108 becomes visible when the hydrocolloid patch 100 reaches a predetermined temperature and is less visible when the hydrocolloid patch 100 is not at the predetermined temperature. This may be achieved, for example, by selecting an initial, inactive color for the thermochromic material 108 that matches the color of outer layer 102 or is not visible on the outer layer 102. In this manner, when the thermochromic material 108 is heated, it becomes activated, changes colors, and the indicator becomes visible.

In other examples, the thermochromic material 108 may provide an indicator that is visible to tell the wearer when the hydrocolloid patch 100 is not at the predetermined temperature. In this case, the thermochromic material 108 may become less visible when the hydrocolloid patch 100 is at the predetermined temperature.

The thermochromic material 108 can also present an alternative indicator in the event the temperature of the hydrocolloid patch 100 exceeds a predetermined temperature. In this manner, the thermochromic material 108 can indicate to the user if the hydrocolloid patch 100 is too hot to be applied to the skin.

The indicator may have many different forms. Examples of types of possible indicators includes words, letters, punctuation, symbols, colors, and the like. The indicator may be any indicator that the wearer can understand indicates a temperature state of the hydrocolloid patch 100.

Figure 6:
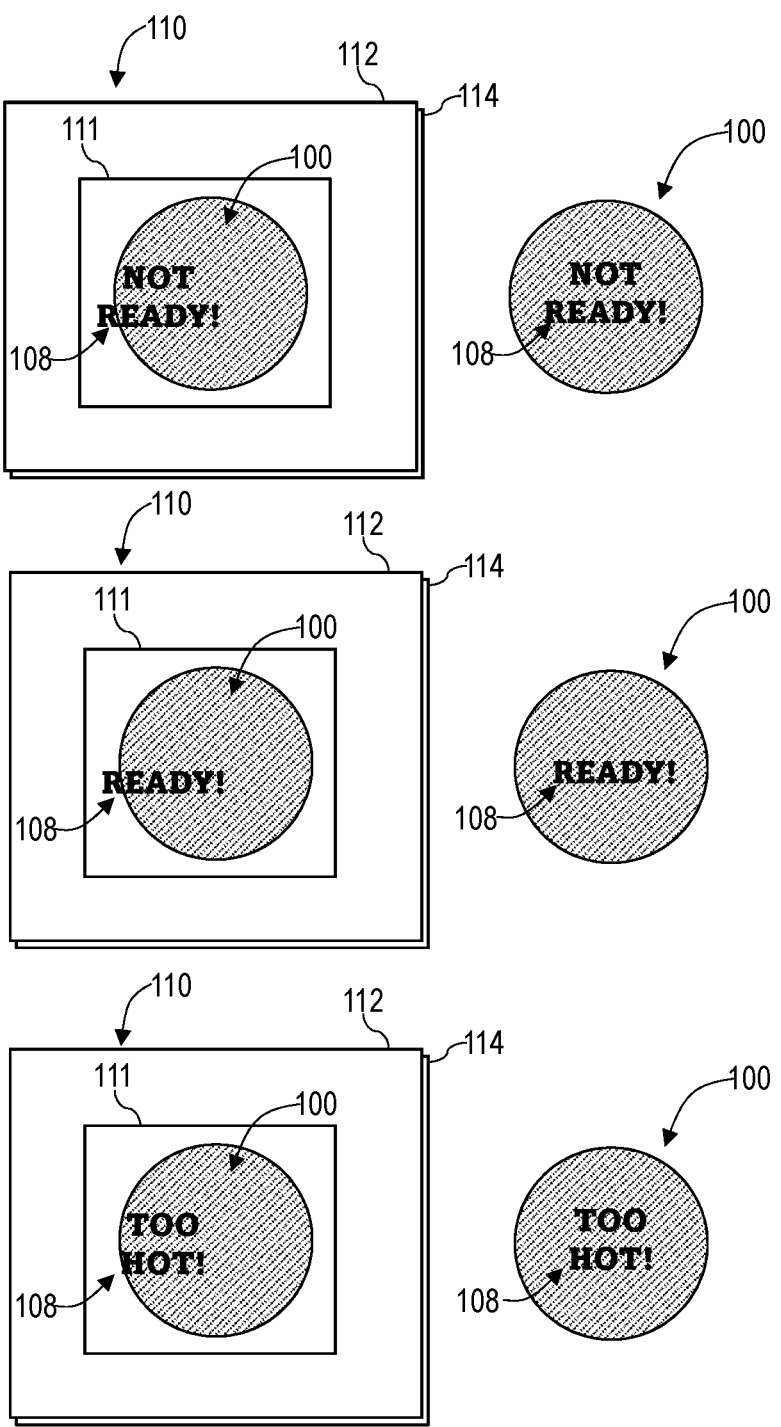
FIG. 6 shows a hydrocolloid patch inside and outside packaging and in different states of heating.

Referring to FIG. 6, the hydrocolloid patch 100 is in packaging 110, such as a wrapper, and the thermochromic material 108 is on the packaging 110. The packaging 110 encapsulates the hydrocolloid patch 100 until it is ready to be used. The packaging 110 includes an upper layer 112 and a lower layer 114 that are attached together along their perimeter and between which the hydrocolloid patch 100 is positioned. The upper layer 112 and lower layer 114 are adhered together. The adhesive is such that the user can peel the upper layer 112 away from the lower layer 114 to remove the hydrocolloid patch 100.

The packaging 110 forms a substantially waterproof barrier around the hydrocolloid patch 100 so that the hydrocolloid patch 100 can be heated by placing the packaging 110 in hot water. As hydrocolloids naturally absorb liquids, the use of waterproof packaging 110 is useful if heating in hot water.

The packaging 110 may be made from packaging material such as acrylic, polyethylene terephthalate, amorphous copolyester, polyvinyl chloride, polycarbonate, cyclic olefin copolymers, polyethylene, or the like.

In the example of FIG. 6, the packaging 110 includes a thermochromic material 108 that changes color when the predetermined temperature is reached. The thermochromic material 108 is applied to the upper layer 112.

As shown in the upper panel of FIG. 6, prior to the packaging 110 being placed in hot water, the thermochromic material 108 indicator may notify the user that the hydrocolloid patch 100 is not at the predetermined temperature or the packaging may have no visible indicator.

As shown in the middle panel of FIG. 6, once the packaging 110 containing the hydrocolloid patch 100 reaches the predetermined temperature, the thermochromic material 108 changes to indicate the hydrocolloid patch 100 patch is at the predetermined temperature and is ready to be placed on the skin.

As shown in the bottom panel of FIG. 6, the thermochromic material 108 may also be used to provide an indicator that notifies the wearer when the hydrocolloid patch 100 is too hot for placement on the skin. This is a safety precaution.

The packaging 110 may be opaque, translucent, or transparent. In the example of FIG. 6, the packaging 110 includes a transparent section 111 through which the hydrocolloid patch 100 is visible. If the hydrocolloid patch includes a thermochromic material 108, the transparent section 111 permits the thermochromic material 108 on the hydrocolloid patch 100 to be visible from outside the packaging 110.

As the hydrocolloid patch 100 is worn on the skin and cools, the thermochromic material 108 may change color to become less visible so as to not have substantially visible indicator while being worn for a long period.

Figure 7:
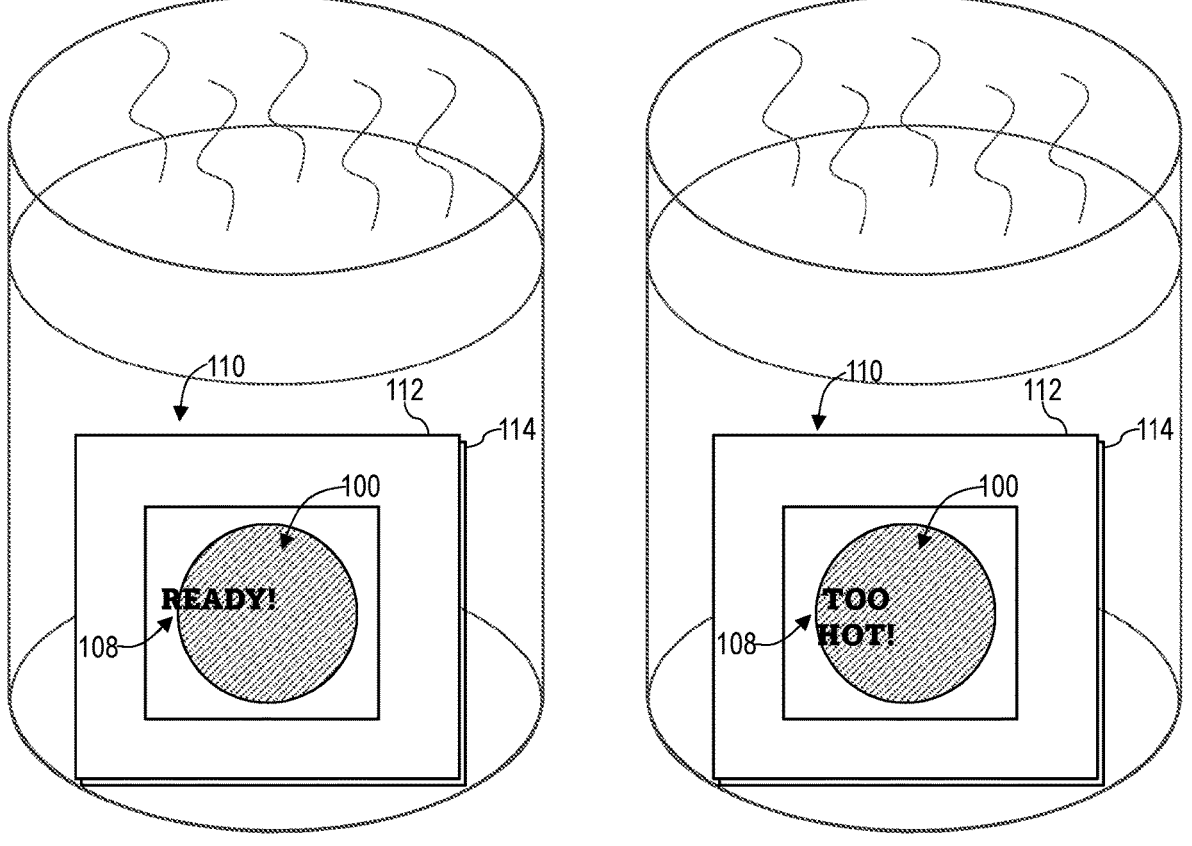
FIG. 7 shows a hydrocolloid patch being heated in hot water. The left panel shows the hydrocolloid patch at the predetermined temperature and indicating it is ready to be applied to skin. The right panel shows the hydrocolloid patch above the predetermined temperature and indicating it is too hot to be applied to skin.

Referring to FIG. 7, the hydrocolloid patch 100 in packaging 110 is placed in hot water in a container. Any container that can be heated and permits the wearer to view the packaging 110 may be used. The packaging 110 protects the hydrocolloid patch 100 from contacting the water through a water-tight seal between the upper layer 112 and lower layer 114. When the packaging 110 achieves a temperature of 90 degrees Fahrenheit, for example, the thermochromic material 108 on the packaging 110 transitions to a color that contrasts with the upper layer 112, revealing the indicator provided by the thermochromic material 108 and indicates that hydrocolloid patch 100 is ready to be removed from the container and applied to the skin of the wearer. As a safety precaution, an additional indicator in a different thermochromic material 108, changes color when the hydrocolloid patch 100 is too hot and may pose a burn risk if applied to the skin. The temperature at which burns can occur according to medical professionals is 105 degrees Fahrenheit. However, in order to create a safe product, at or above 100 degrees Fahrenheit, for example, the thermochromic material 108 can visibly indicate that the product is too hot for use.

Figure 8:
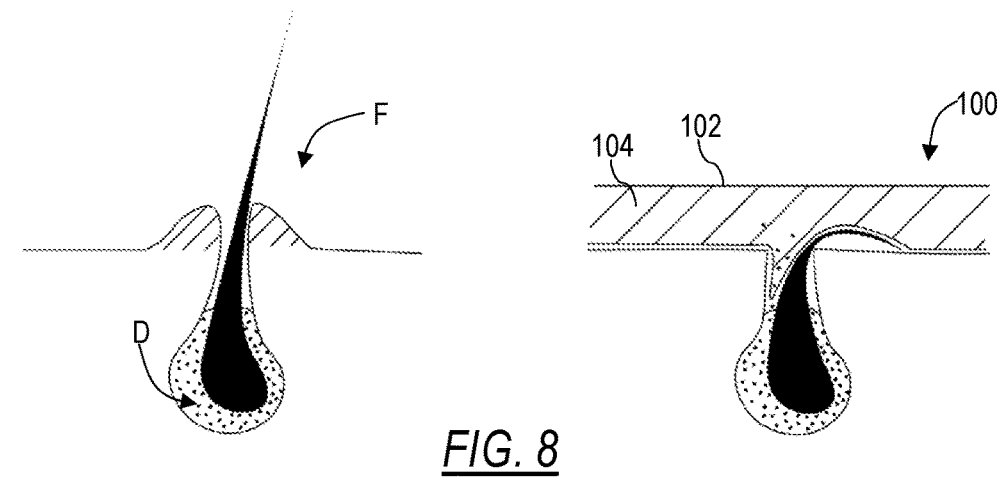
FIG. 8 is a schematic of a hair follicle (left panel) and a hair follicle covered by a hydrocolloid patch (right panel).

Referring to FIG. 8, an inflamed hair follicle F having debris D therein is shown in the left panel. In the right panel, a hydrocolloid patch 100 is adhered to skin over the hair follicle F. A benefit of heating the hydrocolloid patch 100 is that it promotes the expansion of the hair follicle F for loosening the debris D within the hair follicle. The hydrocolloid layer 104, which is formable, may penetrate into the hair follicle F. The same would apply to pores.

Dilating pores and hair follicles allows the hydrocolloid layer 104 assist with healing the blemish. The hydrocolloid layer 104 creates a moist wound healing environment, to promote faster healing. The outer layer 102 provides a physical barrier between the blemish and any cosmetic, such as concealer, that the wearer might also use to cover up the blemish.

Figure 9:
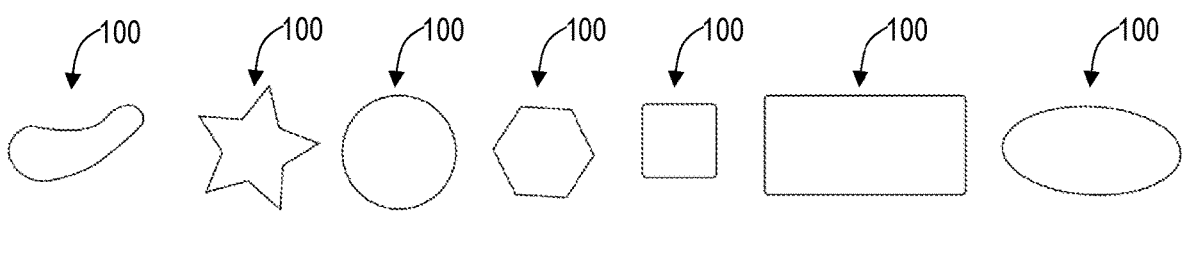
FIG. 9 is a top view of various alternative shapes and sizes for the hydrocolloid patch.

Referring to FIG. 9, the hydrocolloid patch 100 can come in various shapes and size such as the examples shown.

The thermochromic material 108 can likewise be applied to the hydrocolloid patch 100 and/or packaging 110 in various shapes and configurations.

Figure 10:
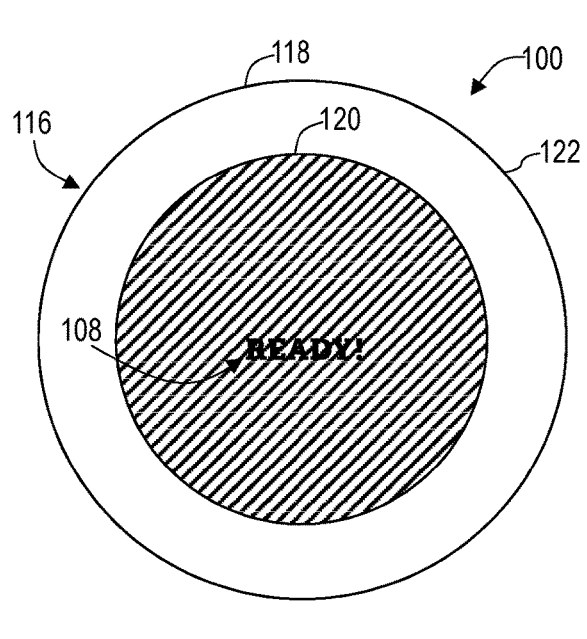
FIG. 10 is a top view of another example of the hydrocolloid patch.

Referring to FIG. 10, another example of the hydrocolloid patch 100 includes an adhesive tape 116, including a plastic film 118 such as a layer of polyethylene, polyurethane, polyester, or the like with an adhesive on the skin contacting side thereof. The adhesive may be an adhesive suitable for skin contact such as acrylic, polydimethylsiloxane, or the like. The tape 116 is joined to the outer layer 102 of the hydrocolloid patch 100 and has a perimeter 122 that extends beyond a perimeter 120 of the hydrocolloid layer 104, creating a border about the hydrocolloid layer 104. Benefits of this example may include greater discretion by permitting better concealment of the hydrocolloid patch 100 when worn, more adhesion to the skin, and to further protect the hydrocolloid layer 104.

Certain examples of the hydrocolloid patch have a thickness of 0.12 mm to 1.5 mm in order to absorb sebum during wear. Since hydrocolloid materials are hydrophilic, they attract water, which draws fluid out of blemishes. As fluids are drawn out of a blemish, dead cells and nutrients may also be absorbed into the hydrocolloid material. The hydrocolloid patch 100 is designed to absorb a large amount of exudate due to its thickness. This is because as fluids are absorbed by the hydrocolloid patch 100, the hydrocolloid patch 100 may become non adherent and detach from the skin.

Figure 11:
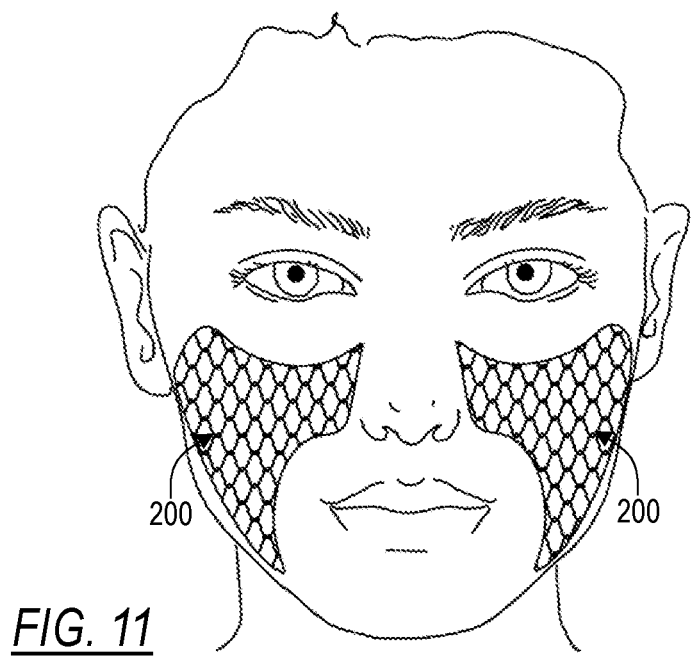
FIG. 11 shows some of the possible locations on the face for the hydrogel patches.

Referring to FIG. 11, the hydrogel patch 200 may be positioned on areas of the face that are prone to being dehydrated. Applying a cold hydrogel patch 200 may promote soft tissue healing, as well as the production of elastin and collagen, which area responsible for tightening the skin. It may also constrict pores. The cold hydrogel patch 200 may also reduce swelling. A cold hydrogel patch 200 may provide a reduce puffiness, reduce excess oil production, manage acne, soothe sunburn, reduce swelling and inflammation, reduce signs of aging, and boost the skin's healthy glow.

Figure 12:
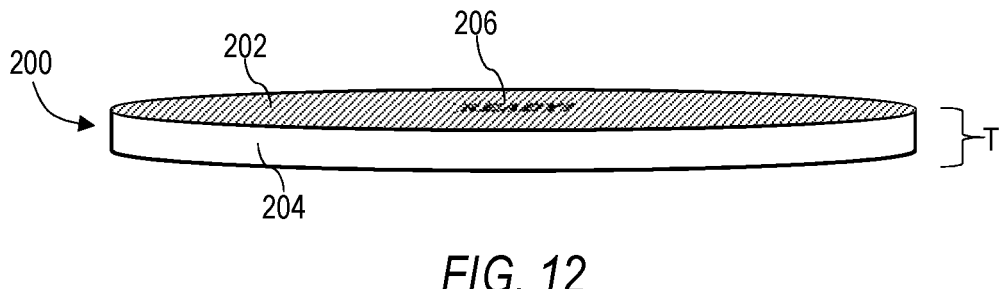
FIG. 12 is a top perspective view of an example of a hydrogel patch.
Figure 13:
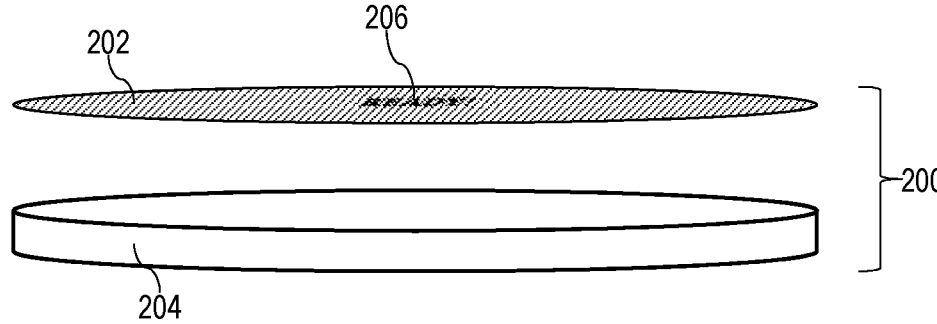
FIG. 13 is an exploded view thereof.

Referring to FIGS. 12 and 13, an example of a hydrogel patch 200 includes an outer layer 202, a hydrogel layer 204, and a thermochromic material 206.

The outer layer 202 covers the underlying hydrogel layer 204 and protects it from external contamination. The outer layer 202 also deters exudate from leaking outside of the hydrogel patch 200.

The outer layer 202 includes a backing material suitable for use in wound dressings. Examples of such backing materials include but are not limited to woven or nonwoven fabrics, knits, films, or the like. Backing materials used in conventional wound dressings may be used.

In certain examples, the backing material may be an opaque, translucent, or transparent polymeric elastic film.

The backing material may be flexible and conformable to different surfaces of the body. When the backing material is applied to the skin, it can conform to the shape of the skin even if the wearer moves. The backing material may be constructed in such a way that it stretches and contracts to adapt to bodily movement.

Examples of specific backing materials include, but are not limited to polyethylene, polyurethane, co-polyester, polyether block amide films, PVC, or the like.

The outer layer 202 may be waterproof and/or may be breathable with a moisture vapor transmission rate above 0%.

The hydrogel layer 204 includes a hydrogel material. The hydrogel material is a hydrophilic and formable substrate which can adhere to skin and may help to absorb fluids during wear.

Hydrogel materials are composed of water in a polymeric gel base. Due to their water content, hydrogels provide a moist environment for wound healing. A hydrogel is a polymer network that is composed of polymers that absorb water and swell. Hydrogels can be prepared by different cross-linking strategies. Hydrogels form a physical barrier over wounds, assist with removing excess exudate from wounds, and provide a moist environment to promote wound healing. Hydrogel materials can sometimes fill irregularly shaped wounds and assist with controlling bleeding.

Examples of polymeric hydrogel materials that may be used include, but are not limited to, polyethylene glycols, keratins, polyvinyl alcohols, chitosans, gelatins, methylcelluloses, ethylcelluloses, hydroxypropyl methyl celluloses, alginates, collagens, polyacrylic acids, polystyrene sulfonates, starches, hyaluronic acids, polyethylene glycol dimethacrylate, peptides, heparins, fibrins, acrylate polymers and copolymers, or the like.

The hydrogel material carries water within the polymer network. In certain examples, the hydrogel material has about 10-70% w/w water content.

The hydrogel material may also include a pressure sensitive adhesive, such as poly-isobutylene, or the like.

The hydrogel material may include one or more anti-freezing agents designed to lower the freezing point of the hydrogel material. Examples of anti-freezing agents include, methanol, sodium chloride, glycerol, ethanol, ethylene glycol, calcium chloride, or the like.

Certain examples of the hydrogel patch 200 have a thickness T of 0.1 mm to 1.5 mm or 0.12 mm to 1.5 mm.

Certain examples of the hydrogel material may also include one or more other ingredients such as, for example, therapeutically active ingredients such as wound healing promoting compounds and antimicrobial compounds. Other ingredients may include beautifying ingredients, such as aloe, hyaluronic acid, peptides, apple cider vinegar, collagen, turmeric, green tea, Vitamin A, Vitamin C, Vitamin E, or any other combination of ingredients.

The hydrogel patch 200 also includes a thermochromic material 206 that reversibly changes color when cooled below a temperature that causes a color or appearance transition in the thermochromic material. Examples of thermochromic materials are discussed above.

Conventional thermochromic inks, thermochromic plastics, thermochromic dyes, thermochromic powders, thermochromic films, or the like may serve as the thermochromic material 206. The purpose of the thermochromic material 206 is to indicate to the wearer when the hydrogel patch 200 is at a predetermined temperature for placement on the skin.

In the example of FIGS. 12 and 13, the thermochromic material 206 is on the outer layer 202 in the form of a visible indicator. This example allows the thermochromic material 206 to convey a message to the wearer when it is ready for application to the skin.

The thermochromic material 206 is selected to provide an indicator relating to the temperature of the hydrogel patch 200. The indicator may be the appearance of a visible indicator, a color change, a thermometer, or the like. The thermochromic material 206 provides the indicator at a predetermined temperature. For example, the predetermined temperature may be above a freezing point of the hydrogel layer 204 to 55 degrees F., or 20-55 degrees F. In other examples, the predetermined temperature may be a temperature in which the hydrogel patch 200 is too cold to be applied to skin.

In certain examples, the thermochromic material 206 becomes visible when the hydrogel patch 200 reaches a predetermined temperature and is less visible when the hydrogel patch 200 is not at the predetermined temperature. This may be achieved, for example, by selecting an initial, inactive color for the thermochromic material 206 that matches the color of outer layer 202 or is not visible on the outer layer 202. In this manner, when the thermochromic material 206 is cooled to a predetermined temperature, it becomes activated, changes color, and the indicator become visible.

In other examples, the thermochromic material 206 may provide a visible indicator to tell the wearer when the hydrogel patch 200 is not at the predetermined temperature. In this case, the thermochromic material 206 may become less visible when the hydrogel patch 200 is at the predetermined temperature.

The thermochromic material 206 can also present an alternative visible indicator in the event the temperature of the hydrogel patch 200 is below a predetermined temperature. In this manner, the thermochromic material 206 can indicate to the user if the hydrogel patch 200 is too cold to be applied to the skin.

The visible indicator may have many different forms. Examples of types of possible visible indicators include one or more words, letters, punctuation, symbols, colors, and the like. The visible indicator may be any indicator that the wearer can understand indicates a temperature state of the hydrogel patch 200.

Figure 14:
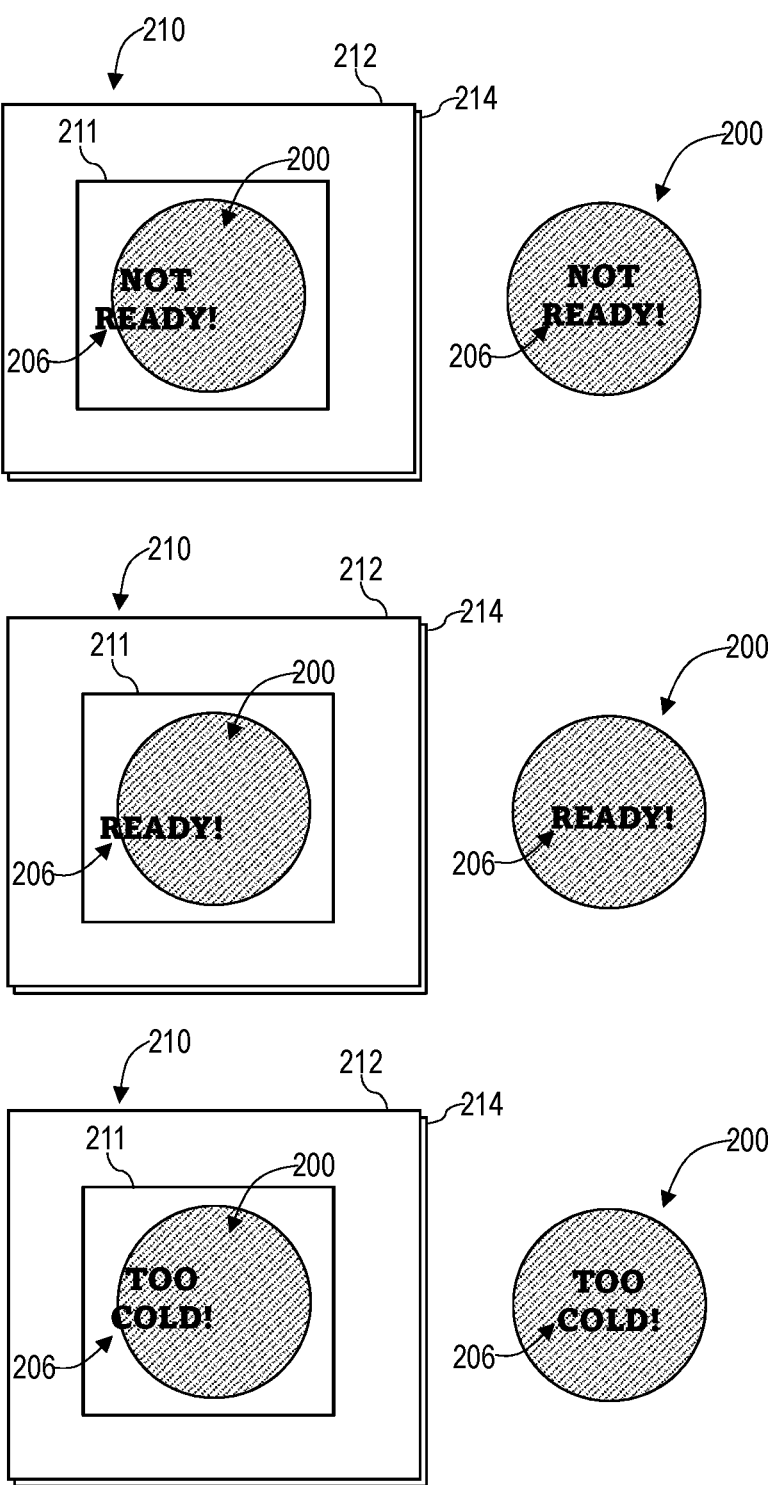
FIG. 14 shows a hydrogel patch inside and outside packaging and in different states of cooling.

Referring to FIG. 14, the hydrogel patch 200 is in packaging 210, such as a wrapper, and the thermochromic material 206 is on the packaging 210. The packaging 210 encapsulates the hydrogel patch 200 until it is ready to be used. The packaging 210 includes an upper layer 212 and a lower layer 214 that are attached together along their perimeters and between which the hydrogel patch 200 is positioned. The upper layer 212 and lower layer 214 are adhered together. The adhesive is such that the user can peel the upper layer 212 away from the lower layer 214 to remove the hydrogel patch 200.

The packaging 210 forms a substantially waterproof barrier around the hydrogel patch 200 so that the hydrogel patch 200 can be cooled by placing the packaging 210 in a cold environment such as an ice bath, a refrigerator, a freezer, or the like. The substantially waterproof barrier also limits the water in the hydrogel from evaporating and causing the hydrogel to become stiff and dehydrated.

In the example of FIG. 14, the packaging 210 includes a thermochromic material 206 that changes color when the predetermined temperature is reached. The thermochromic material 206 is applied to the upper layer 212.

As shown in the upper panel of FIG. 14, prior to the packaging 210 being cooled, the thermochromic material 206 indicator may notify the user that the hydrogel patch 200 is not at the predetermined temperature or the packaging may have no visible indicator.

As shown in the middle panel of FIG. 14, once the packaging 110 containing the hydrogel patch 200 is cooled to the predetermined temperature, the thermochromic material 106 changes color to indicate the hydrogel patch 200 is at the predetermined temperature and is ready to be placed on the skin.

As shown in the bottom panel of FIG. 14, the thermochromic material 206 may also be used to provide a visible indicator that notifies the wearer when the skin patch 200 is too cold for placement on the skin.

The thermochromic material 206 may also be used to provide a visible indicator that notifies the wearer when the hydrogel patch 200 is too cold for placement on the skin.

The packaging 210 may be opaque, translucent, or transparent. In the example of FIG. 14, the packaging 210 includes a transparent section 211 through which the hydrogel patch 200 is visible. If the skin patch 200 includes a thermochromic material 206, the transparent section 211 permits the thermochromic material 206 on the hydrogel patch 200 to be visible from outside the packaging 200.

The packaging 210 may be made from packaging material such as acrylic, polyethylene terephthalate, amorphous copolyester, polyvinyl chloride, polycarbonate, cyclic olefin copolymers, polyethylene, or the like.

The hydrogel patch 200 may be used for cosmetic purposes and/or medical purposes by medical professionals. In a professional setting, such as cryotherapy, temperatures of negative 140 degrees Fahrenheit, for example, are used.

As the cold hydrogel patch 200 is worn against the skin, it warms and reaches homeostasis. At this stage, the thermochromic material 206 may change color to become less visible so as to not have a substantially visible indicator while being worn for a long period.

The hydrogel patch 200 with the packaging 210 may be cooled using many different types of cooling techniques such as ice baths, refrigeration, or the like.

Figures 15, 16, 17:
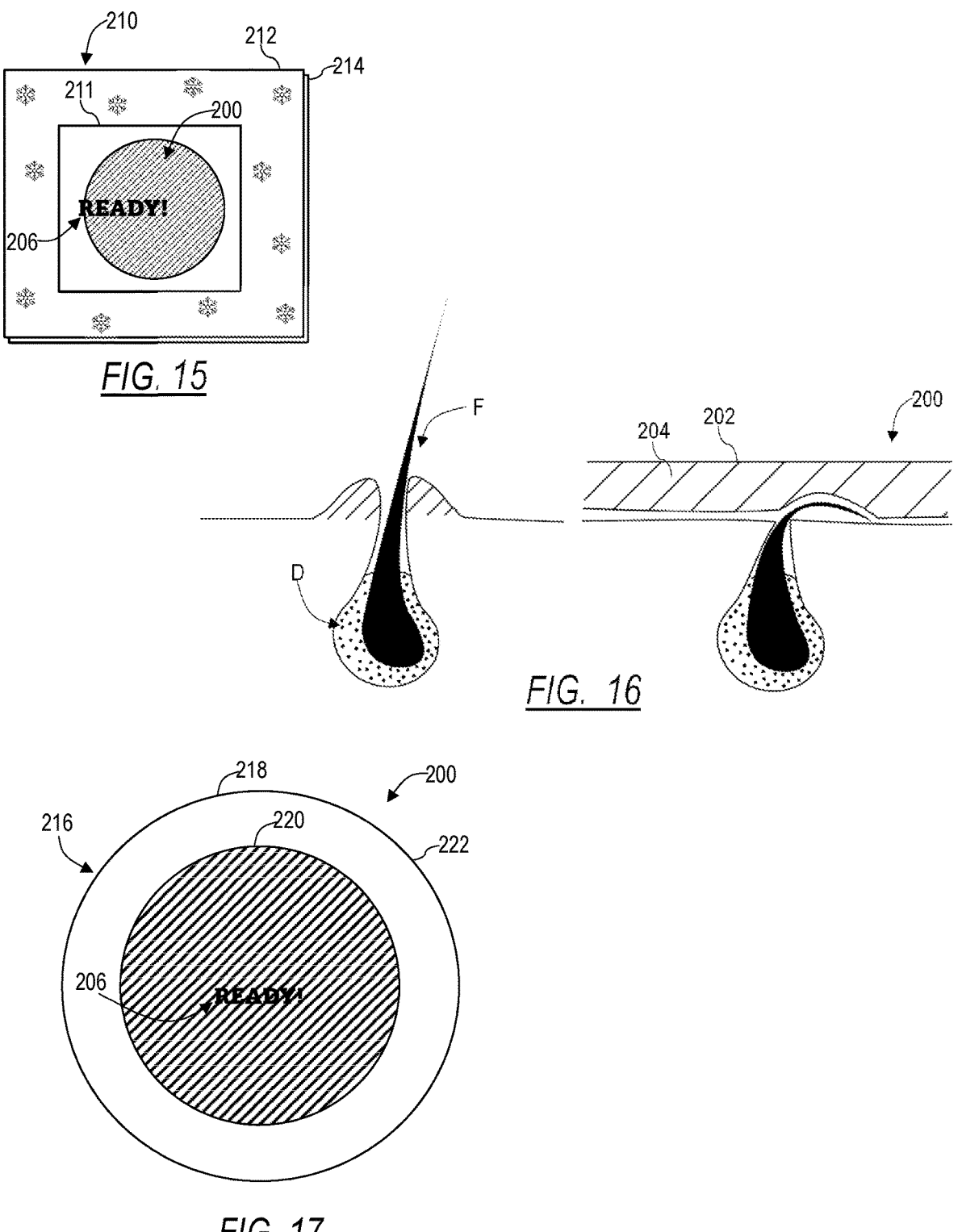
FIG. 15 is an illustration of the hydrogel patch in a cold state.
FIG. 16 shows a human face with a blemish (left panel) and with the blemish covered by a hydrogel patch (right panel).
FIG. 17 is a top view of another example of the hydrogel patch.

In FIG. 15, the hydrogel patch 200 has been cooled to a predetermined temperature in a freezer, which chills the hydrogel patch 200 to a temperature that matches the freezer temperature, such as at or below 0 degrees C. As depicted, the thermochromic material 206 is on the packaging 210. Since the packaging 210 is substantially waterproof, this protects the hydrogel patch 200 and prevents potential contamination or condensation from reaching the hydrogel patch 200 and potentially altering the skin patch's 100 performance.

FIG. 16 is a schematic of a hair follicle F with debris therein (left panel) and a hair follicle F covered by a hydrogel patch 200 (right panel). A benefit of cooling the hydrogel patch 200 and placing it on a blemish such as an inflamed hair follicle is that the cold hydrogel patch 200 may reduce swelling, inflammation, redness, and pain.

Using a cold hydrogel patch 200 may also shrink the size of pores such that bacteria and contamination will have difficulty entering pores to further aggravate the blemish. Also, the hydrogel layer 204 creates a moist wound healing environment, such that the wound may heal faster. A benefit of the outer layer 202 is to provide a barrier between the wound and any introduced cosmetics, such as concealer, that might aggravate the blemish, while at the same time allowing the wearer to cover up the blemish.

The hydrogel patch 200 may sometimes be positioned in locations where excess oil production is prevalent. After washing the face to clear a pore of dirt and debris, the hydrogel patch 200 may be applied in order to decrease the size of the pore or help heal the blemish, reducing the chance of bacteria colonization and clogging of the pore. The cold hydrogel patch 200 may decrease inflammation in the area around the blemish and may reduce pain associated with irritation. Since the hydrogel layer 204 is formable, the hydrogel patch 200 can provide significant coverage over the blemish. Constricting pores may reduce further contamination, thus aiding in the healing process. Additionally, the cold hydrogel patch 200, may increase blood circulation in the area of application, promoting soft tissue healing.

Cosmetics such as makeup may be applied over the outer layer 202.

The hydrogel patch 200 can come in various shapes and sizes other than the examples shown.

The thermochromic material 206 can likewise be applied to the hydrogel patch 200 and/or packaging 210 in various shapes and configurations.

Referring to FIG. 17, another example of the hydrogel patch 200 includes an adhesive tape 216, including a plastic film 218 such as a layer of polyethylene, polyurethane, polyester, or the like with an adhesive on the skin contacting side thereof. The adhesive may be an adhesive suitable for skin contact such as acrylic, polydimethylsiloxane, or the like. The tape 216 is joined to the outer layer 202 of the hydrogel patch 200 and has a perimeter 222 that extends beyond a perimeter 220 of the hydrogel layer 204, creating a border about the hydrogel layer 204. Benefits of this example may include greater discretion by permitting better concealment of the hydrogel patch 200 when worn, more adhesion to the skin, and further protection of the hydrogel layer 204.

Referring to FIG. 18, the silicone patch 300 is designed to be placed in areas for which signs of aging such as wrinkles, skin darkening, and skin thinning may occur. Silicone patches 300 may also be used to fade and flatten scars. When a silicone patch 300 is applied to skin, it creates a substantially moisture occlusive barrier with a moisture vapor transmission rate of about 0%. This may increase blood flow to the area and make the skin perspire from its bottom layer. As the moisture raises to the surface of the skin it may activates the fibroblasts and promote collagen synthesis.

The silicone patch 300 may include an outer layer similar to that of the hydrocolloid patch 100 and hydrogel patch 200 as described above. This outer layer may be over a silicone layer.

Silicone is also substantially non-damaging to fragile areas of skin, such as under the eyes. Silicone is adhesive, but it does not permanently stick to skin cells, oils or any other aspects of the skin and can be reposition and washed. This is because silicone is hydrophobic.

The silicone patch 300 may include a conventional silicone adhesive such as polydimethylsiloxane or the like. Certain examples of the silicone patch 300 have a thickness between 0.1 to 1.5 mm or 0.12 mm and 1.5 mm, for example.

Referring to FIG. 19, another example of a silicone patch 300 that may be included in the product 10 is shaped to be placed around the front of the neck to reduce the appearance of wrinkles.

Referring to FIG. 20, another example of the silicone patch 300 includes an adhesive tape 316, including a plastic film 318 such as a layer of polyethylene, polyurethane, polyester, or the like with an adhesive on the skin contacting side thereof. The adhesive may be an adhesive suitable for skin contact such as acrylic, polydimethylsiloxane, or the like. The tape 316 is joined to the outer layer of the silicone patch 300 and has a perimeter 322 that extends beyond a perimeter 320 of the silicone layer, creating a border about the silicone layer. Benefits of this example may include greater discretion by permitting better concealment of the silicone patch 300 when worn, more adhesion to the skin, and further protection of the silicone layer 304.

The facial patch product may be modified in many different ways without departing from the scope of what is claimed. The scope of the claims is not limited to the particular features and examples described above.

That which is claimed is:

1. A method comprising:
   placing on a first portion of a human face a hydrocolloid patch having a hydrocolloid patch outer layer that forms a physical barrier over a hydrocolloid layer attached to the hydrocolloid patch outer layer;
   placing on a second portion of the human face a hydrogel patch having a hydrogel patch outer layer that forms a physical barrier over a hydrogel layer attached to the hydrogel patch outer layer;
   placing on a third portion of the human face a silicone patch; and
   wearing the hydrocolloid patch, hydrogel patch, and silicone patch at the same time.

2. The method of claim 1, wherein a first thermochromic material on the hydrocolloid patch and/or first waterproof packaging encapsulating the hydrocolloid patch indicates the hydrocolloid patch is at a predetermined temperature.

3. The method of claim 2, wherein the first thermochromic material is on the hydrocolloid patch outer layer.

4. The method of claim 2, wherein the first thermochromic material is on the first waterproof packaging.

5. The method of claim 2, wherein the first thermochromic material is on the hydrocolloid patch and the first waterproof packaging includes a transparent section through which the first thermochromic material is visible from outside the first waterproof packaging.

6. The method of claim 2, wherein the predetermined temperature is 80 to 100 degrees F.

7. The method of claim 2, wherein the predetermined temperature is 105 degrees F.

8. The method of claim 2, wherein the first thermochromic material is on the first waterproof packaging encapsulating the hydrocolloid patch, the first waterproof packaging having an upper layer and a lower layer that are attached together along a perimeter thereof.

9. The method of claim 2, wherein the first thermochromic material indicates whether the hydrocolloid patch is too hot for safe application to skin.

10. The method of claim 2, wherein the first thermochromic material indicates whether the hydrocolloid patch is below the predetermined temperature, at the predetermined temperature, and above the predetermined temperature.

11. The method of claim 1, wherein a second thermochromic material on the hydrogel patch and/or second waterproof packaging encapsulating the hydrogel patch indicates the hydrogel patch is at a predetermined temperature.

12. The method of claim 11, wherein the second thermochromic material is on the second waterproof packaging.

13. The method of claim 11, wherein the second thermochromic material is on the hydrogel patch and the second waterproof packaging includes a transparent section through which the second thermochromic material is visible from outside the second waterproof packaging.

14. The method of claim 11, wherein the predetermined temperature is 20 to 55 degrees F.

15. The method of claim 11, wherein the second thermochromic material is on the second waterproof packaging encapsulating the hydrogel patch and the hydrogel patch is cooled in the second waterproof packaging.

16. The method of claim 11, wherein the second thermochromic material is on the second waterproof packaging encapsulating the hydrogel patch, the second waterproof packaging having an upper layer and a lower layer that are attached together along a perimeter thereof.

17. The method of claim 11, wherein the second thermochromic material indicates whether the hydrogel patch is too cold for application to skin.

18. The method of claim 11, wherein the second thermochromic material indicates whether the hydrogel patch is below the predetermined temperature, at the predetermined temperature, and above the predetermined temperature.

19. The method of claim 11, wherein the hydrogel patch includes at least one freezing point lowering agent configured to lower a freezing point of the hydrogel selected from methanol, ethanol, calcium chloride, sodium chloride, glycerol, and ethylene glycol.

20. The method of claim 1, wherein the hydrogel patch includes a material that decreases a freezing point of water in the hydrogel layer.

21. The method of claim 1, wherein a thermochromic material is on waterproof packaging encapsulating the hydrocolloid patch and the hydrocolloid patch is heated by heating the waterproof packaging encapsulating the hydrocolloid patch in hot water.

22. The method of claim 1, wherein the hydrocolloid patch includes at least one water boiling point elevating agent selected from calcium chloride, sodium chloride, and acetic acid.

23. The method of claim 1, wherein the hydrocolloid patch includes a hydrocolloid layer configured to adhere to skin and a waterproof outer layer over the hydrocolloid layer.

24. The method of claim 1, further comprising, before placing the hydrocolloid patch on the first portion of the human face, heating the hydrocolloid patch in waterproof packaging in hot water until a thermochromic material on the waterproof packaging indicates the hydrocolloid patch is at a predetermined temperature.

25. The method of claim 1, further comprising, before placing the hydrogel patch on the second portion of the human face, cooling the hydrogel patch in waterproof packaging until a thermochromic material on the waterproof packaging indicates the hydrogel patch is at a predetermined temperature.

26. The method of claim 1, further comprising:

before placing the hydrocolloid patch on the first portion of the human face, heating the hydrocolloid patch in a first waterproof packaging in hot water until a first thermochromic material on the first waterproof packaging indicates the hydrocolloid patch is at a first predetermined temperature; and before placing the hydrogel patch on the second portion of the human face, cooling the hydrogel patch in a second waterproof packaging until a second thermochromic material on the second waterproof packaging indicates the hydrogel patch is at a second predetermined temperature.

* * * * *